(12) United States Patent  (10) Patent No.: US 7,918,819 B2
Karmarkar et al.  (45) Date of Patent: Apr. 5, 2011

(54) VARIABLE CURVE CATHETER

(75) Inventors: Parag Karmarkar, Columbia, MD (US); Robert J. Lederman, Chevy Chase, MD (US)

(73) Assignee: Health & Human Services - NIH, Bethesda, MD (US)

( * ) Notice: Subject to any disclaimer, the term of this patent is extended or adjusted under 35 U.S.C. 154(b) by 1539 days.

(21) Appl. No.: 10/534,362

(22) PCT Filed: Nov. 14, 2003

(86) PCT No.: PCT/US03/36210
§ 371 (c)(1),
(2), (4) Date: Nov. 7, 2005

(87) PCT Pub. No.: WO2004/045672
PCT Pub. Date: Jun. 3, 2004

(65) Prior Publication Data
US 2006/0142732 A1   Jun. 29, 2006

(51) Int. Cl.
*A61M 31/00* (2006.01)
(52) U.S. Cl. .................................... 604/95.01
(58) Field of Classification Search .... 604/95.01–95.04, 604/523–533
See application file for complete search history.

(56) References Cited

U.S. PATENT DOCUMENTS

| 3,856,009 | A | * | 12/1974 | Winnie |
| 4,512,765 | A | * | 4/1985 | Muto ............................ 604/119 |
| 4,935,017 | A | * | 6/1990 | Sylvanowicz |
| 4,976,688 | A | * | 12/1990 | Rosenblum |
| 5,004,455 | A | * | 4/1991 | Greenwood et al. |
| 5,231,989 | A | * | 8/1993 | Middleman et al. |
| 5,318,525 | A | * | 6/1994 | West et al. ................. 604/95.04 |
| 5,381,782 | A | * | 1/1995 | DeLaRama et al. .......... 600/149 |
| 5,454,787 | A | * | 10/1995 | Lundquist .................. 604/95.01 |
| 5,538,512 | A | * | 7/1996 | Zenzon et al. |
| 5,709,874 | A | * | 1/1998 | Hanson et al. |
| 5,833,632 | A | * | 11/1998 | Jacobsen et al. ............. 600/585 |
| 5,876,373 | A | * | 3/1999 | Giba et al. ................. 604/95.04 |
| 6,053,900 | A | * | 4/2000 | Brown et al. |
| 6,592,581 | B2 | * | 7/2003 | Bowe .............................. 606/41 |
| 7,455,657 | B2 | * | 11/2008 | Naimark et al. |

* cited by examiner

*Primary Examiner* — Manuel A Mendez
(74) *Attorney, Agent, or Firm* — Edwards Angell Palmer & Dodge LLP; Peter F. Corless; Lisa Swiszcz

(57) ABSTRACT

Disclosed is a deflectable tip guiding device, such as a catheter, that enables a physician, or other health care personnel, to vary the radius of curvature of the tip of the device. In one embodiment, a guiding device includes an elongate body and a deflectable distal tip. An elongate stiffener tube is coupled to the body for longitudinal movement relative thereto and has a distal end spaced a variable distance from the distal end of the tip, thereby serving as a fulcrum for the tip. Longitudinal movement of the stiffener tube relative to the body varies the distance between the distal ends of the tip and tube, which in turn causes a corresponding increase or decrease in the radius of curvature of the tip.

44 Claims, 2 Drawing Sheets

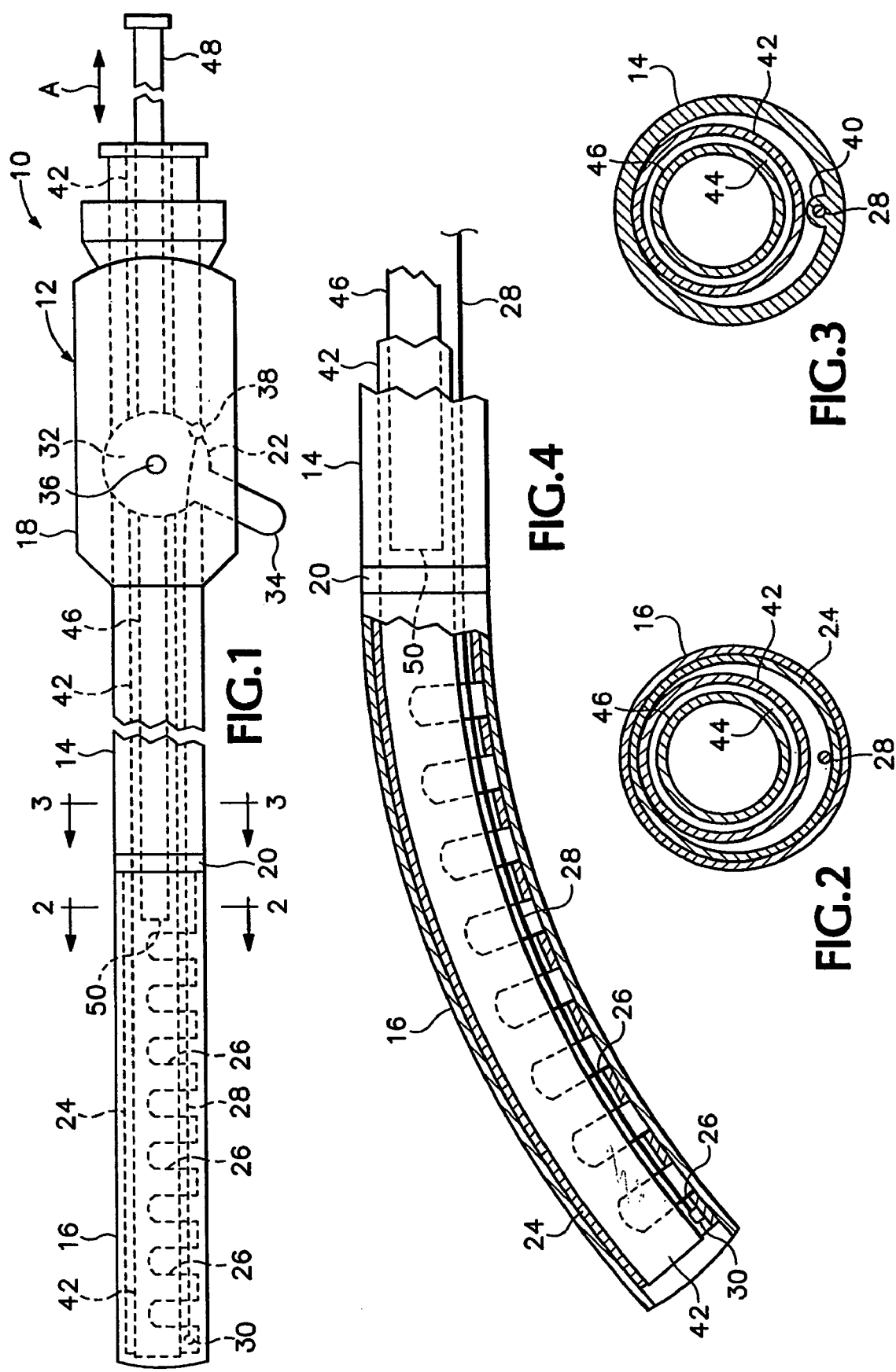

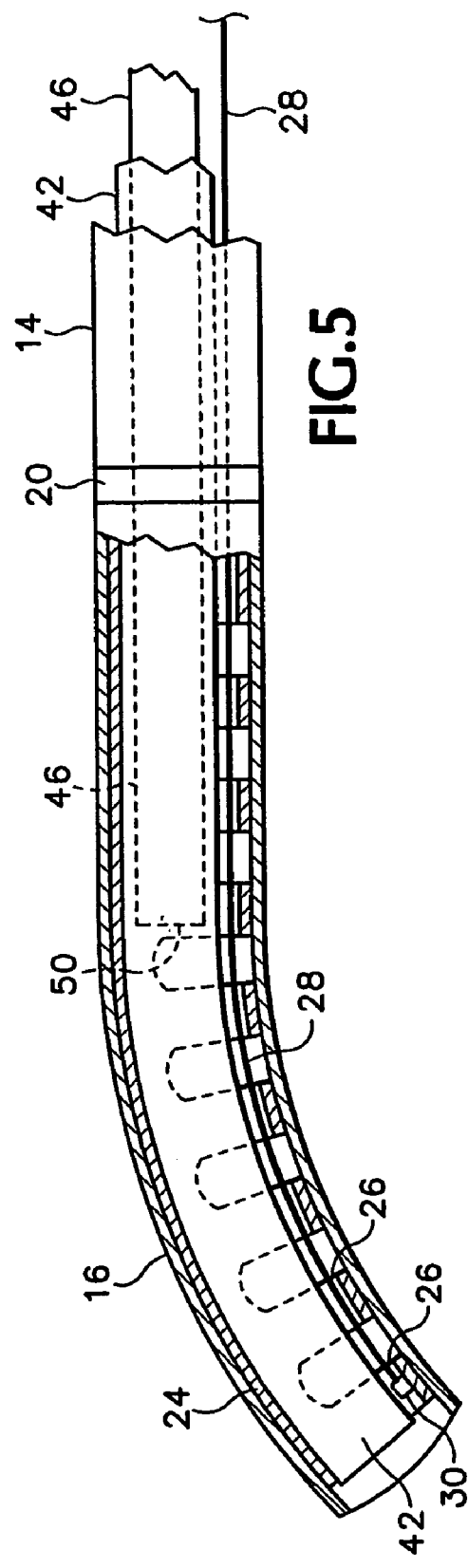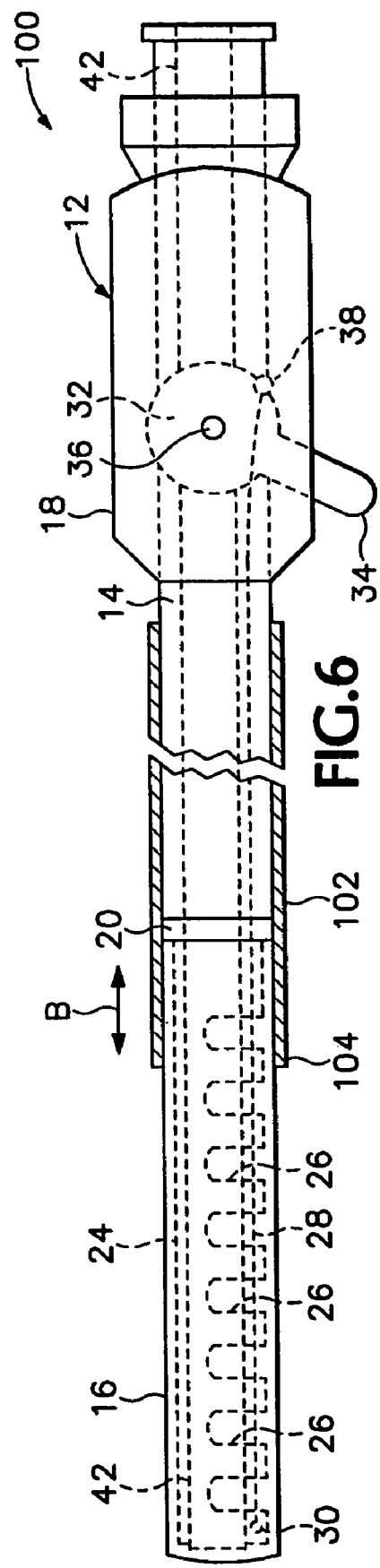

VARIABLE CURVE CATHETER

FIELD

The present invention relates to medical devices, such as surgical catheters. In particular, the present invention relates to catheters having deflectable tips.

BACKGROUND

Minimally invasive therapeutic surgical procedures are increasingly applied as alternatives to open surgical treatments. Exemplary minimally invasive surgeries, include transcatheter and laparascopic treatments and similar percutaneous surgeries. Such procedures are often guided by devices having a steerable or deflectable tip, or distal section, such as gastrointestinal endoscopes and myocardial injection or ablation guiding catheters. A conventional deflectable catheter typically has an elongate body and a flexible tip, or distal section, connected to the distal end of the body. One or more pull wires extend from the distal end of the tip to a control mechanism at the proximal end of the body. A control knob allows for selective pulling of the pull wires to cause the tip of the catheter to deflect in one or more directions.

Such classic (or "fixed-fulcrum") deflectable-tip devices have limited degrees of freedom because the tips have fixed radii of curvature. In this regard, the length of the deflectable section of their distal tip mainly depends on the length of the distal deflection mechanism. In a myocardial injection catheter, for example, a fixed-fulcrum device would have limited ability to reach all myocardial walls from a single transaortic approach. Another drawback of the fixed-fulcrum design is that, because the tip, or distal section, has a fixed radius of curvature, navigating the device through a tortuous passageway within a body can be difficult.

Accordingly, there exists a need for new and improved guiding devices and methods for their use.

SUMMARY

To this end, and according to one embodiment, a deflectable guiding device, such as a catheter, enables a physician, or other health care personnel, to vary the radius of curvature of the tip of the device, even when the device is positioned in, or is being steered through, the body of a patient.

Generally speaking, one embodiment of the guiding device has a deflectable tip, or distal section, but the fulcrum for the deflector mechanism can be axially displaced to permit the operator to vary the radius of curvature. In this manner, the length (or "reach") of the deflectable segment can be varied to enable access of or navigation along more complex trajectories. A prototypical application of the device is as a myocardial injection guiding catheter. Such a device enables better direct access to all endomyocardial walls from a transaortic approach. In comparable applications, such as a endolumen-traversal system or neolumen-creation device, this moving-fulcrum deflector permits a more comprehensive ability to navigate complex geometric pathways.

In particular embodiments, a guiding device includes an elongate body and a distal section coupled to the body, with the distal section being deflectable upon application of an external force by an operator. A longitudinally extending inner lumen, adapted to deliver a therapeutic agent or device into a subject, is defined by the body and the tip. The device also includes a curvature-adjustment mechanism, which allows an operator to adjust the radius of curvature and the length of the distal section.

In some embodiments, the curvature-adjustment mechanism comprises an elongate stiffener tube that is longitudinally slidable relative to the body. The tube has a distal end spaced a variable distance from the distal end of the deflectable tip, thereby serving as a fulcrum for the tip. Longitudinal movement of the stiffener tube relative to the body varies the distance between the distal ends of the tip and tube that, in turn, causes a corresponding increase or decrease in the radius of curvature of the tip. In an illustrated embodiment, the stiffener tube extends through the lumen and is formed with an internal bore for delivering therapeutic agents through the device. In another illustrated embodiment, the stiffener tube is an outer sleeve concentrically disposed on and slidable relative to the body and tip.

The guiding devices described herein have a deflectable length of the distal section that can be varied from about 20 cm to about 0.5 cm. Further, the guiding devices can be made compatible with magnetic resonance imaging (MRI) and other imaging methods and an imaging antenna can be built into it to enable active tracking under MRI.

The foregoing and other features and advantages will become more apparent from the following detailed description of several embodiments, which proceeds with reference to the accompanying figures.

BRIEF DESCRIPTION OF THE DRAWINGS

FIG. 1 is a schematic side view of a catheter in accordance with one embodiment.

FIG. 2 is an enlarged cross-sectional view of the catheter taken along line 2-2 of FIG. 1.

FIG. 3 is an enlarged cross-sectional view of the catheter taken along line 3-3 of FIG. 1.

FIG. 4 is an enlarged schematic view of the distal tip of the catheter of FIG. 1, shown partially in section and illustrating the operation of the catheter.

FIG. 5 is a view similar to FIG. 4 showing the curvature-adjustment mechanism after it is moved to a more distal position to provide the distal tip with a smaller radius of curvature than shown in FIG. 4.

FIG. 6 is a schematic side view of a catheter according to another embodiment.

DETAILED DESCRIPTION

The singular forms "a," "an," and "the" refer to one or more than one, unless the context clearly indicates otherwise. For example, the term "comprising a lumen" includes single or plural lumen and is considered equivalent to the phrase "comprising at least one lumen."

The term "or" refers to a single element of stated alternative elements or a combination of two or more elements. For example, the phrase "a chemical or mechanical agent" refers to a chemical agent, a mechanical agent, or both a chemical agent and a mechanical agent.

The term "comprises" means "includes." Thus, "comprising a catheter and a pull wire" means "including a catheter and a pull wire," without excluding additional elements.

As used herein, the term "proximal" refers to a portion of an instrument closer to an operator, while "distal" refers to a portion of the instrument farther away from the operator.

The term "subject" refers to both human and other animal subjects. In certain embodiments, the subject is a human or other mammal such as a primate, cat, dog, cow, horse, rodent, sheep, goat, or pig.

The term "distal tip" also refers to the "distal section" of the catheter.

Referring to FIG. 1, there is shown a catheter 10 according to one embodiment. The catheter 10 includes a handle 12, an elongate catheter tube, or body, 14 extending distally from the handle 12, and an elongate deflectable, or steerable, distal end portion (also referred to as a distal section or tip), 16 extending distally from the body 14.

The body 14 and distal section, or tip, 16 can be made from any suitable material, or combination of materials, that provide both the strength and flexibility desired. Exemplary materials include, but are not limited to: polymers, such as polyethylene or polyurethane; carbon fiber; or metals, such as Nitinol®, platinum, titanium, tungsten, stainless steel, MP35N, copper, or nickel. The body and/or tip optionally can be reinforced with fibers of metal, carbon fiber, glass, fiberglass, a rigid polymer, or other high-strength material. In particular embodiments, the body and/or tip material is compatible with an imaging system, device, or method, such as magnetic resonance imaging (MRI), ultrasound, or fluoroscopy. Exemplary materials include braided Nitinol®, platinum, tungsten, MP35N, or surgical stainless steel. Additionally, the exterior surfaces of the body and/or tip can be coated with a material or substance, such as Teflon® or other lubricious material, that aids in the insertion of the body and/or tip into the subject and/or aids in the movement of the body and/or tip through the subject.

The body and/or tip also can contain features that aid in imaging the position of the body and/or tip within the subject, such as radioopaque markers to enhance visualization by fluoroscopy, MRI or X-ray, or etched grooves to enhance visualization by ultrasound imaging. Additionally, the device itself can contain its own visualization device, such as a fiber optic cable having a lens at its distal end and connected to a video camera and display unit at its proximal end. Exemplary self-contained visualization devices include endoscopic or artheroscopic visualization systems, such as these disclosed in U.S. Pat. No. 5,860,992, which can be adapted for use with the system described herein.

The body 14 can be generally rigid to resist deflection or can be flexible so that it can assume a non-linear shape as the catheter is inserted into a subject. Movement of the tip 16 can be controlled by an operator, as described below.

An annular lubricating strip 20 is disposed on the tip 16 adjacent the distal end of the body. Lubricating strip 20 is composed of a hydrophilic or lubricious material, such as Teflon® to facilitate movement of catheter 10 through a subject's body, such as through the vasculature of a subject's body.

Cross-sectional views of the distal section, or tip, 16 and the body 14 are shown in FIGS. 2 and 3, respectively. While the body 14 and tip 16 in the illustrated embodiment exhibit a circular cross-sectional profile, alternative embodiments could employ a body and/or tip having a differently shaped cross-section, such as a square, oval, elliptical, rectangular, or triangular cross-section.

The catheter 10 in the illustrated configuration includes a flexible slotted tube 24 extending at least through the distal tip 16 of the catheter 10. The slotted tube 24 is formed with a plurality of slots 26 on one side and spaced longitudinally along the length of the tube 24. This plurality of slots 26 facilitates the deflection of tip 16 in at least two ways. Each slot 26 offers a collapsible space that can reduce the resistance of flexible slotted tube 24 to bending. Additionally, the plurality of slots 26 helps to direct tip 16 along the axis of deflection induced when pull wire 28 is retracted, pulling back on the distal end of slotted tube 24 at anchor point 30. For example, when pull wire 28 is retracted, one component of the force of retraction lies in the distal-proximal direction (for example, from left to right in FIG. 1) and another component of the force of retraction lies perpendicular to this distal-proximal direction (for example, downward in FIG. 1), since anchor point 30 is attached to an edge of slotted tube 4 (rather than its center) adjacent its distal end, as can be seen in the illustrated embodiments. Thus, the force of rectraction is offset from the longitudinal axis of catheter 10 (for example, downward and to the right in FIG. 1). If slotted tube 24 was a contiguous piece, rather than formed with the plurality of slots 26, the material of slotted tube 24 would offer compression resistance against the force of retraction. However, the spaces of slots 26 can be considered points of no resistance that reduce the compression resistance of slotted tube 24 to the retraction force of pull wire 28. The force of retraction encounters reduced opposed compression resistance along the direction of slots 26, and distal tip 16 of catheter 10 deflects along this direction of least resistance.

The handle 12 includes a housing 18 that encloses a suitable control mechanism (also referred to herein as a steering mechanism), such as the illustrated control knob 22. Housing 18 also serves as a grip or handhold for the user. Control knob 22 includes a cam mechanism 32 mounted on shaft 36 within the housing 18. A lever 34 connected to the cam mechanism 32 extends laterally of the housing 18. The catheter 10 has at least one pull wire 28 for controlling deflection of the distal tip 16. As shown in FIG. 1, one end of the pull wire 28 is connected to the distal end of the slotted tube 24 at 30, and the opposite end of the pull wire 28 is connected to the cam mechanism 32 at 38. As shown in FIG. 3, pull wire 28 extends through a lumen defined by a projection 40 formed on the inner surface of the body 14. Pull wire 28 can be a flexible stainless steel wire or any of various other materials. Other control or steering mechanisms are suitable, however, such as those described in the PCT Publication WO 96/35469.

Rotation of the cam mechanism 32 causes a corresponding deflection of the tip 16. As can be appreciated from FIG. 1, the illustrated embodiment is configured such that counterclockwise rotation of cam mechanism 32 pulls the pull wire 28 toward the handle, which causes a corresponding downward deflection of the distal tip 16 (FIGS. 4 and 5). While one form of a control mechanism is shown for the purposes of illustration, various other mechanisms may be used to apply forces to the pull wire 28 for controlling the deflection of the distal tip 16.

A flexible inner tube 42 is positioned within and extends longitudinally through the body 14 and tip 16. An inner lumen 44, extending along the length of the catheter 10, is defined by tube 42 and a corresponding hole (not shown) extending longitudinally through the housing 18. In particular embodiments, tube 42 is open at the distal end of the tip 16. In this manner, inner lumen 44 serves as a conduit for introducing an agent into a subject as described below.

The catheter 10 also includes a curvature-adjustment mechanism for enabling a user to vary the radius of curvature of the tip 16. In the illustrated embodiment, for example, the curvature-adjustment mechanism is an elongate tube 46 (also referred to herein as a stiffener tube or element) slidably received in the inner lumen 44. The proximal end portion 48 of tube 46 extends outwardly from the proximal end of the handle 12 to permit a user to slide the tube 46 either distally (toward the tip 16) or proximally (away from the tip 16), as indicated by double-headed arrow A in FIG. 1. Tube 46 can be made from polymeric, metallic, or any of various other suitable materials, and can exhibit an axial rigidity (stiffness) that is constant or varies along its length.

Tube 46 can exhibit a bending stiffness that is greater than the combined bending stiffness of the distal tip 16, slotted tubing 24 and inner tube 42 so that the tube 46 remains substantially undeflected when pull wire 28 is tensioned to deflect tip 16. In this manner, the distal end 50 of tube 46 serves as a fulcrum for the tip, defining the curvature assumed by the tip 16 when tension is applied to pull wire 28. Hence, the radius of curvature of the tip 16 can be varied by adjusting the longitudinal position of tube 46 along the length of the catheter. For example, in FIG. 4, tube 46 is positioned so that its distal end 50 is located in the body 14 adjacent insulating strip 20 so that when tension is applied to pull wire 28, the tip 16 assumes a relatively large radius of curvature. However, when the tube 46 is moved to a more distal position, as shown in FIG. 5, the tip 16 assumes a non-linear shape having a smaller radius of curvature.

FIG. 6 shows a catheter 100 according to another embodiment, in which components that are similar to corresponding components in the embodiment of FIGS. 1-5 have the same respective reference numerals. Catheter 100 is similar to catheter 10 shown FIGS. 1-5, with the exception that catheter 100 has a curvature-adjustment mechanism in the form of a rigid outer sleeve 102 disposed on the body 14 and tip 16, rather than the stiffener tube illustrated in FIGS. 1-5. Sleeve 102 is slidable longitudinally relative to the body 14 and tip 16, as indicated by double-headed arrow B, to allow an operator to adjust the longitudinal position of the sleeve 102. Sleeve 102, like tube 46 of the embodiment shown in FIGS. 1-5, has a bending stiffness that is substantially greater than the combined bending stiffness of the distal tip 16, slotted tubing 24 and inner tube 42, so that the sleeve 102 remains substantially undeflected when tension is applied to pull wire 28. The distal end 104 of the sleeve 102 provides a fulcrum for the tip 16 so that varying the longitudinal position of the sleeve 102 causes a corresponding increase or decrease of the radius of curvature of the tip 16.

The device 10,100 is capable of delivering a diagnostic, prophylactic or therapeutic agent to an anatomic structure (a tissue, organ, cavity, space, or other structure) within the body of a subject, such as the heart. The agent may be a solid, liquid, gas, or radiation, and may be a pharmaceutical, chemical, biological, mechanical, or radiant energy agent. Suitable diagnostic, prophylactic, and therapeutic agents include, but are not limited to, the particular agents disclosed herein.

Pharmaceutical agents include drugs commonly available to treat disease, such as pro-angiogenic agents, pain relievers, anti-cancer agents, antibiotics, anti-thrombotic agents, antivirals, and enzymatic inhibitors. Chemical agents include non-pharmaceutical chemicals, such as ethanol, phenol, chelating agents, ablative agents and contrast agents for imaging particular structures of the body, including contrast agents for X-ray, fluoroscopy, ultrasound, computerized tomography (CT), and MRI. Biological agents include nucleic acids, amino acids, proteins, glycoproteins, proteoglycans, polypeptides, polymer formulations of biological agents, autologous cells, allogeneic cells, xenogeneic cells, stem cells, endothelial progenitor cells, ex-vivo expanded cells, bone marrow cells, viruses, prions, biochemicals, vitamins, and hormones. Mechanical agents include mechanisms for monitoring, visualizing, or manipulating internal portions of a body, including thermometers and other sensors, cameras, probes, needles, knives, electrocautery snares, biopsy forceps, and suction tubes. Radiant energy agents include acoustic, thermal, and electromagnetic energies, such as infrared, thermal, x-ray, microwave, radiofrequency, ultrasound, cryogens, and laser. In some embodiments, plural agents are mixed or delivered together. As just one, non-limiting example, ethanol (an ablative agent) can be mixed with a contrast agent, such as microbubbles for sonographic contrast, iodinated radiocontrast for X-ray contrast, or a metal chelate for MRI contrast.

For example, in one embodiment, the inner lumen 44 is adapted to receive a drug delivery system, such as disclosed in U.S. Pat. No. 6,346,099.

Other features and aspects of the guiding device disclosed herein are as follows:

Transluminal device delivery into a variety of tissues including heart, arteries, veins and lymphatics; oropharynx and bronchial tree; genitourinary system including urethra, bladder, ureters, and renal pelvis; gastrointestinal lumens including digestive and biliary tracts; central nervous system including cerebrospinal ventricles and cisterns; tissue and fascial planes and other potential spaces for minimally invasive procedures.

Some embodiments offer tip deflection with four degrees of freedom: axial displacement, axial rotation, tip deflection, and variable length of deflecting tip.

Other embodiments include multiple deflectors and multiple fulcrums arranged in series for additional degrees of freedom.

The fulcrum can be displaced using a variety of replaceable shafts altering the stiffness of the primary shaft.

Particular embodiments can be used to deliver therapeutics (including proteins and small molecules); nucleic acids (including plasmid DNA, viral vectors); cells (such as putative stem and progenitor cells); energy (such as radiofrequency, laser, ultrasound, and cryoablative); and tension or apposition-delivery devices such as sutures and staples.

When a mechanical agent is used, the mechanical agent initially may be situated within the longitudinally extending inner lumen and is positioned proximally to an anatomical structure at a distance suitable for functionality of the mechanical agent. The mechanical agent then may be advanced from the inner lumen toward the anatomical structure, manipulated as needed, and then activated.

Other particular embodiments can be used for receive diagnostic information such as reflective light or ultrasound or temperature or video images or radiofrequency or electromagnetic energy.

Some embodiments can have small profile for small target organs or devices, while other embodiments have a large profile for large target organs or devices.

Fulcrum-displacement can be within or without the main guiding catheter, delivering other diagnostic or therapeutic devices or agents, and can be coaxial or non-coaxial.

The present invention has been shown in the described embodiments for illustrative purposes only. The present invention may be subject to many modifications and changes without departing from the spirit or essential characteristics thereof. We therefore claim as our invention all such modifications as come within the spirit and scope of the following claims.

We claim:

1. A catheter comprising:
    an elongate body;
    a distal section coupled to the body;
    a deflection mechanism comprising a pull wire operatively connected to the distal section, wherein the distal section is deflectable upon application of an external force by a user via the pull wire, and wherein the distal section is linear absent application of an external force by a user via the pull wire;

a longitudinally extending inner lumen defined by the body and the tip, the lumen being adapted to deliver a diagnostic, prophylactic, or therapeutic agent into a subject;

a curvature-adjustment mechanism configured to adjust the radius of curvature of the distal section by providing a variable fulcrum for the distal section.

2. The catheter of claim 1, wherein the curvature-adjustment mechanism comprises an elongate stiffener tube that is slidable longitudinally relative to the body, the elongate stiffener tube providing a fulcrum spaced a distance from the distal end of the distal section, the distance being variable by longitudinal movement of the curvature-adjustment mechanism to vary the radius of curvature of the distal section.

3. The catheter of claim 2, wherein the stiffener tube is concentrically disposed on the body.

4. The catheter of claim 2, wherein the stiffener tube extends through the body.

5. The catheter of claim 2, wherein the stiffener tube comprises a sleeve disposed on the outside of the body.

6. The catheter of claim 1, wherein said distal section comprises a slotted tube formed with a plurality of slots spaced longitudinally along one side of said slotted tube.

7. The catheter of claim 6, wherein said slots provide collapsible spaces between longitudinally spaced portions of the slotted tube on opposite sides of the slots to reduce resistance to bending.

8. The catheter of claim 6, wherein the pull wire is operatively connected to the distal end portion of said slotted tube on said one side of said slotted tube.

9. The catheter of claim 8, wherein said pull wire extends longitudinally of said elongate body toward a proximal end portion of said elongate body to permit a user to longitudinally shift said pull wire to control deflection of said slotted tube.

10. The catheter of claim 6, wherein said curvature-adjustment mechanism comprises an elongate stiffener tube that is slidable longitudinally relative to said slotted tube to provide a fulcrum spaced a distance from the distal end of the distal section, the distance being variable by longitudinal movement of the curvature-adjustment mechanism to vary the radius of curvature of the distal section.

11. The catheter of claim 10, wherein said stiffener tube is concentrically disposed relative to the slotted tube.

12. The catheter of claim 10, wherein the stiffener tube extends into the interior of said slotted tube.

13. The catheter of claim 10, wherein the stiffener tube comprises a sleeve disposed exteriorly of the said slotted tube.

14. The catheter of claim 6, wherein said distal section comprises a flexible outer tube surrounding said slotted tube.

15. A catheter comprising:

an elongate body, a distal section coupled to the body, a deflection controlling mechanism, wherein the distal section is operatively connected to the deflection controlling mechanism such that the distal section is deflectable upon application of an external force by a user on the deflection controlling mechanism, the distal section comprising an elongate flexible outer tube and an elongate slotted tube having a plurality of slots spaced longitudinally along one side of said slotted tube, with said slotted tube extending longitudinally through a major portion of said outer tube, a longitudinally extending inner lumen defined by the body and distal section adapted to deliver a diagnostic, prophylactic, or therapeutic agent into a subject, and a curvature-adjustment mechanism configured to adjust the radius of curvature of the distal section comprising an elongate stiffener tube which is slidable longitudinally relative to the body, the curvature-adjustment mechanism providing a fulcrum spaced a distance from the distal end of the distal section, with said distance being variable by longitudinal movement of the stiffener tube to vary the radius of curvature of the distal section.

16. The catheter of claim 15, wherein the stiffener tube is concentrically disposed relative to said body.

17. The catheter of claim 15, wherein the stiffener tube extends through the body.

18. The catheter of claim 15, wherein the stiffener tube comprises a sleeve disposed on the outside of the body.

19. The catheter of claim 15, wherein said slots provide collapsible space between portions of the slotted tube on opposite sides of the slots to minimize resistance to bending.

20. The catheter of claim 15, wherein the deflection controlling mechanism comprises a pull wire operatively connected to a distal end portion of said slotted tube on said one side of said slotted tube.

21. The catheter of claim 20, wherein said pull wire extends longitudinally of said elongate body toward a proximal end portion of said elongate body to permit longitudinal shifting of said pull wire to control deflection of said slotted tube.

22. A method of delivering a therapeutic agent into a subject comprising:

positioning a catheter according to claim 1 or 15 proximal to an anatomic structure of a subject; wherein the longitudinally extending inner lumen of said catheter includes a therapeutic agent, ejecting a therapeutically sufficient amount of said therapeutic agent from said inner lumen onto said anatomical structure, thereby effecting the treatment of said anatomical structure with said therapeutic agent.

23. The method according to claim 22 wherein said anatomical structure is a tissue.

24. The method according to claim 23 wherein said tissue is selected from a group consisting of an artery, vein, lymphatic duct, oropharynx bronchial tree, digestive tract, biliary tracts and central nervous system.

25. The method according to claim 22 wherein said anatomical structure is an organ.

26. The method according to claim 25 wherein said organ is the heart.

27. The method according to claim 25 wherein said organ is selected from a group consisting of a urethra, bladder, ureter, and renal pelvis.

28. The method according to claim 22 wherein said anatomical structure is a cavity and wherein the ejecting step delivers the therapeutic agent within said cavity.

29. The method according to claim 22 wherein said anatomical structure is a space and wherein the ejecting step delivers the therapeutic agent within said space.

30. The method according to claim 22 wherein said therapeutic agent has a phase selected from the group consisting of a solid, liquid and gas.

31. The method according to claim 22 wherein said therapeutic agent is radiation.

32. The method according to claim 22 wherein said therapeutic agent is a pharmaceutical agent selected from the group consisting of pain relievers, anti-cancer agents, antibiotics, anti-thrombotic agents, antivirals, and enzymatic inhibitors.

33. The method according to claim 22 wherein said therapeutic agent is a chemical agent selected from the group consisting of ethanol, phenol, a chelator, an ablative agent, and a contrast agent for imaging.

34. The method according to claim 22 wherein said therapeutic agent is a biologically active agent selected from the group consisting of a nucleic acid, amino acid, proteins, glycoproteins, proteoglycans, polypeptides, polymer formulations of biological agents, autologous cells, allogeneic cells, xenogeneic cells, stem cells, endothelial progenitor cells, ex-vivo expanded cells, bone marrow cells, whole cells, viruses, prions, biochemicals, vitamins, and hormones.

35. The method according to claim 22 wherein said therapeutic agent is radiant energy selected from the group consisting of acoustic, thermal, and electromagnetic energies.

36. A method of delivering a mechanical agent into a subject comprising:
positioning a catheter according to claim 1 or 15 which includes a mechanical agent within the longitudinally extending inner lumen proximally to an anatomic structure of a subject at a distance suitable for the functionality of said mechanical agent,
advancing said mechanical agent from said inner lumen toward said anatomical structure,
manipulating said mechanical agent, and
actuating said mechanical agent.

37. The method according to claim 36 wherein said anatomical structure is a tissue.

38. The method according to claim 37 wherein said tissue is selected from a group consisting of an artery, vein, lymphatic duct; oropharynx bronchial tree, digestive tract, biliary tracts and central nervous system.

39. The method according to claim 36 wherein said anatomical structure is an organ.

40. The method according to claim 39 wherein said organ is the heart.

41. The method according to claim 39 wherein said organ is selected from a group consisting of a urethra, bladder, ureter, and renal pelvis.

42. The method according to claim 36 wherein said anatomical structure is a cavity.

43. The method according to claim 36 wherein said anatomical structure is a space.

44. The method according to claim 36 wherein said mechanical agent is selected from a group consisting of a thermometer, sensor, camera, probe, needle, knife, electrocautery snare, biopsy forcep, and suction tube.

* * * * *